US010159572B2

United States Patent
Bailey et al.

(10) Patent No.: US 10,159,572 B2
(45) Date of Patent: Dec. 25, 2018

(54) THREADED AUGMENTABLE ACETABULAR SHELL WITH AUGMENTS

(71) Applicant: Biomet Manufacturing, LLC, Warsaw, IN (US)

(72) Inventors: Kirk J. Bailey, Rochester, IN (US); Christopher Peters, Murray, UT (US); Adolph V. Lombardi, New Albany, OH (US); Stephanie Klunk, Hamilton, OH (US); Aaron P. Smith, Warsaw, IN (US); Keith R. Berend, Columbus, OH (US)

(73) Assignee: Biomet Manufacturing, LLC, Warsaw, IN (US)

( * ) Notice: Subject to any disclaimer, the term of this patent is extended or adjusted under 35 U.S.C. 154(b) by 0 days.

(21) Appl. No.: 15/142,740

(22) Filed: Apr. 29, 2016

(65) Prior Publication Data

US 2016/0317307 A1 Nov. 3, 2016

Related U.S. Application Data

(60) Provisional application No. 62/154,326, filed on Apr. 29, 2015.

(51) Int. Cl.
*A61F 2/30* (2006.01)
*A61F 2/34* (2006.01)

(52) U.S. Cl.
CPC ...... *A61F 2/30734* (2013.01); *A61F 2/30724* (2013.01); *A61F 2/34* (2013.01); *A61F 2002/30405* (2013.01); *A61F 2002/30736* (2013.01); *A61F 2002/3401* (2013.01)

(58) Field of Classification Search
CPC .......... A61F 2/34; A61F 2/28; A61F 2/30744; A61F 2/30734; A61F 2/30724
See application file for complete search history.

(56) References Cited

U.S. PATENT DOCUMENTS

| | | |
|---|---|---|
| 5,176,711 A | 1/1993 | Grimes |
| 5,282,861 A | 2/1994 | Kaplan |
| | (Continued) | |

FOREIGN PATENT DOCUMENTS

| | | |
|---|---|---|
| CN | 107979994 A | 5/2018 |
| EP | 0120595 A1 | 10/1984 |
| | (Continued) | |

OTHER PUBLICATIONS

"International Application Serial No. PCT/US2016/030130, International Search Report dated Aug. 2, 2016", 4 pgs.

(Continued)

*Primary Examiner* — Jason-Dennis Stewart
(74) *Attorney, Agent, or Firm* — Schwegman Lundberg & Woessner, P.A.

(57) ABSTRACT

An acetabular prosthesis is described that includes a shell having an outer surface and an inner surface, the outer surface defining an external shape. There is at least one through bore extending from the outer surface of the shell to the inner surface of the shell. At least one augment is configured to be positioned at least partially within the at least one through bore of the shell such that, in an assembled state, the shell and the at least one augment define a modified external shape.

15 Claims, 8 Drawing Sheets

(56) References Cited

U.S. PATENT DOCUMENTS

| | | | |
|---|---|---|---|
| 2007/0106391 A1* | 5/2007 | Ronk | A61B 17/1666 623/22.21 |
| 2007/0173948 A1* | 7/2007 | Meridew | A61F 2/4609 623/22.24 |
| 2010/0057217 A1* | 3/2010 | Breimesser | A61F 2/30744 623/22.34 |
| 2014/0180431 A1* | 6/2014 | Conway | A61B 17/8066 623/22.24 |
| 2015/0005892 A1* | 1/2015 | Meridew | A61F 2/34 623/22.36 |

FOREIGN PATENT DOCUMENTS

| | | |
|---|---|---|
| EP | 0314951 A1 | 5/1989 |
| FR | 2803740 A1 | 7/2001 |
| WO | WO-2016176580 A1 | 11/2016 |

OTHER PUBLICATIONS

"International Application Serial No. PCT/US2016/030130, Written Opinion dated Aug. 2, 2016", 5 pgs.
Levine, Brett R, et al., "Experimental and clinical performance of porous tantalum in orthopedic surgery", Biomaterials, (27), (Sep. 2006), 4671-81.
"International Application Serial No. PCT/US2016/030130, International Preliminary Report on Patentability dated Nov. 9, 2017", 7 pgs.
"European Application Serial No. 16725270.9, Response filed Aug. 6, 2018 to Office Action dated Jan. 30, 2018", 15 pgs.

\* cited by examiner

THREADED AUGMENTABLE ACETABULAR SHELL WITH AUGMENTS

CLAIM OF PRIORITY

This patent application claims the benefit of U.S. Provisional Patent Application Ser. No. 62/154,326, entitled "THREADED AUGMENTABLE SHELL," filed on Apr. 29, 2015, which is hereby incorporated by reference herein in its entirety.

FIELD

This disclosure relates to prosthetic implants, and particularly to an acetabular prosthesis of an implantable acetabular hip prosthesis that is well-suited for use in acetabular revision surgery.

BACKGROUND

The replacement of joints, such as a shoulder, hip, knee, ankle or wrist, with prosthetic implants has become widespread. One problem commonly encountered by surgeons replacing joints is a void or defect in a bone, such as a rim or cavitary defect. Such voids and defects may be caused by natural deterioration of bony tissue surrounding the joint due to natural processes, such as infections, and/or trauma. Developmental problems (e.g., congenital dysplasia of the hip) may also produce voids or defects in the area. Defects in a bone adjacent a joint, such as the hip, shoulder or knee, can also occur due to arthritis of the joint, or following removal of a failed prosthetic implant.

Total hip arthroplasty is a well-known and recognized procedure. A typical procedure involves replacing the top portion of the femur, including the head of the femur which serves as the "ball" in the ball-and-socket joint. Replacement of the socket is typically accomplished by fixing an acetabular component in a surgically prepared natural socket. The acetabular component is a substantially hemispherical cup or shell that is designed to receive a ball-shaped head of a femoral prosthesis component. Fixation of the acetabular component within the surgically prepared natural acetabulum is vital to the long-term success of the procedure, and is typically accomplished by use of bone screws, bone cement, bone ingrowth processes, or a combination of these and/or other techniques.

OVERVIEW

This section provides a general summary of the disclosure, and is not a comprehensive disclosure of its full scope or all of its features.

Because bone defects adjacent joints are quite common, various methods have been proposed for minimizing the adverse effects of such bone defects on joint replacement procedures. Specifically in acetabular revision surgeries, after a failed prosthetic has been removed, orthopedic surgeons generally use large segments of cadaveric bone graft in conjunction with known acetabular components to reconstruct the acetabulum of a patient in which voids or defects are present. However, replacing bone loss and gaining rigid fixation in joint replacement procedures, such as acetabular revision procedures, can be a difficult problem to address, for which there is no universal solution.

The inventors have recognized, among other things, that there is a need for alternative prosthetic implants, such as hip prosthetics, that do not rely on the use of large amounts of bone graft. The inventors have also recognized that there is a need for prosthetic implants that can be individualized or customized to address certain issues of a particular patient's anatomy, such as due to bone loss or other defects. The present subject matter can help provide a solution to this problem by providing an individualized or customizable acetabular prosthesis that can be used for acetabular revision surgery, for example. The individualized or customizable acetabular prosthesis can be assembled in an operating room to match a patient's anatomy and be able to gain fit and fixation in complex acetabular revision cases. The inventors have also recognized that the present subject matter can be applied to implantable replacement prostheses for joints other than the hip, such as other ball-and-socket joints, like the shoulder joint, for example.

An acetabular prosthesis is described that includes a shell having an outer surface and an inner surface, the outer surface defining an external shape. There is at least one through bore extending from the outer surface of the shell to the inner surface of the shell. At least one augment is configured to be positioned at least partially within the at least one through bore of the shell such that, in an assembled state, the shell and the at least one augment define a modified external shape.

Further areas of applicability will become apparent from the detailed description provided herein. The detailed description and specific examples in this summary are intended for purposes of illustration only and are not intended to limit the scope of the present disclosure.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Example embodiments will now be described more fully with reference to the accompanying drawings.

Figure 1:
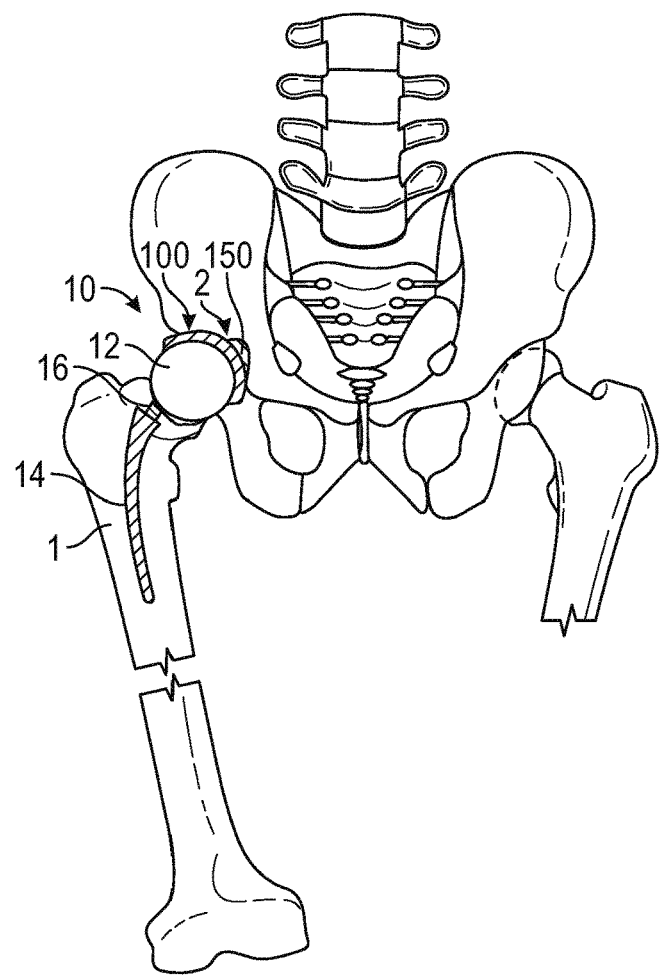
FIG. 1 is a simplified illustration of a human hip joint including an illustrative hip joint prosthesis including an acetabular prosthesis according to at least one example of the present disclosure.

FIG. 1 illustrates a human hip joint having a hip joint prosthesis 10 implanted therein including an acetabular prosthesis 100 according to at least one example of the present disclosure. The hip joint prosthesis 10 can be implanted as shown near a proximal end of a femur 1. The hip joint prosthesis 10 can include a head component 12, a stem component 14, and a neck component 16 that can provide a coupling interface between the head 12 and stem 14 components to connect the head 12 and stem 14 components. The hip joint prosthesis 10 shown is merely exemplary, and other such hip prostheses are also contemplated. For example, the head component 12 can be connected directly to the stem component 14. The head component 12 and the stem component 14 can be part of any suitable hip implant system, such as the TAPERLOC® Hip System sold by Zimmer Biomet, Inc.

The head component 12 can have a generally spherical shape. The head component 12 can be formed of any suitable biocompatible metal, ceramic, or a combination thereof. The stem component 14 can be generally shaped such that it has a length that extends into the femur 1, and a shape that helps fasten the stem component 14 to the femur 1. The hip joint prosthesis 10 can also include acetabular component or prosthesis 100, which is the subject of the present disclosure. The acetabular prosthesis 100 can have a generally conventional dome-shaped configuration with a generally hemi-spherical outer profile intended to be fixed in a hip socket or acetabulum 2, and an inner profile intended for receiving a femoral head 12. As shown, the acetabulum 2 in the figure can have an irregularity due to bone loss. The acetabular prosthesis 100, as shown, can utilize an augment, such as the exemplary augment 150, configured to fit into the area of bone loss and stabilize the acetabular prosthesis 100 in the acetabulum 2.

Acetabular prostheses can be secured in place at an implant site with a suitable cement, an interference fit, or by using bone screws. Gaining rigid fixation of an acetabular component to a hip socket can be important to the longevity of a hip implant system. The method used for affixation can be dictated by conditions that exist at the implant site, such as bone defects. Generally speaking, a surgeon should evaluate the conditions that vary from recipient to recipient, and select the appropriate method of affixation. Since the evaluation may not be completed with accuracy prior to the start of the implant procedure, the surgeon may perform the evaluation during the course of the procedure. Accordingly, it can be important to have different acetabular prostheses available to the surgeon during the procedure that are suited for different methods of fixation and different acetabulum conditions, thus requiring a relatively expensive inventory of acetabular prostheses to be maintained for use in connection with a single procedure. The present subject matter can help provide a solution to the problem of maintaining a large, expensive inventory of acetabular prostheses by providing an individualized or customizable acetabular prosthesis that can be assembled in an operating room to match a patient's anatomy in complex acetabular revision cases.

In various examples, an acetabular prosthesis and its components, including a shell portion and various augments, are discussed below and illustrated in FIGS. 2-13.

Figure 2:
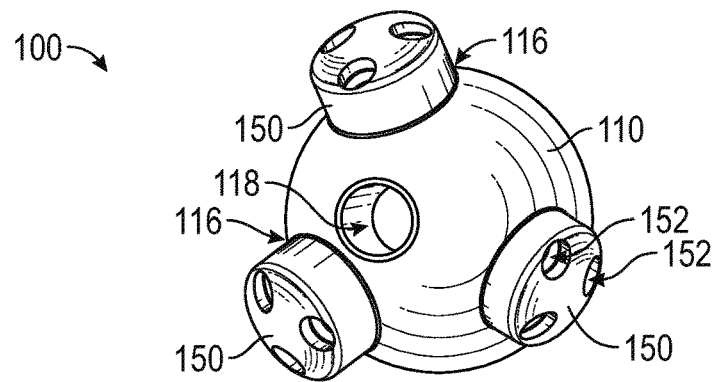
FIG. 2 is a backside view of an acetabular prosthesis according to at least one example of the present disclosure.
Figure 3:
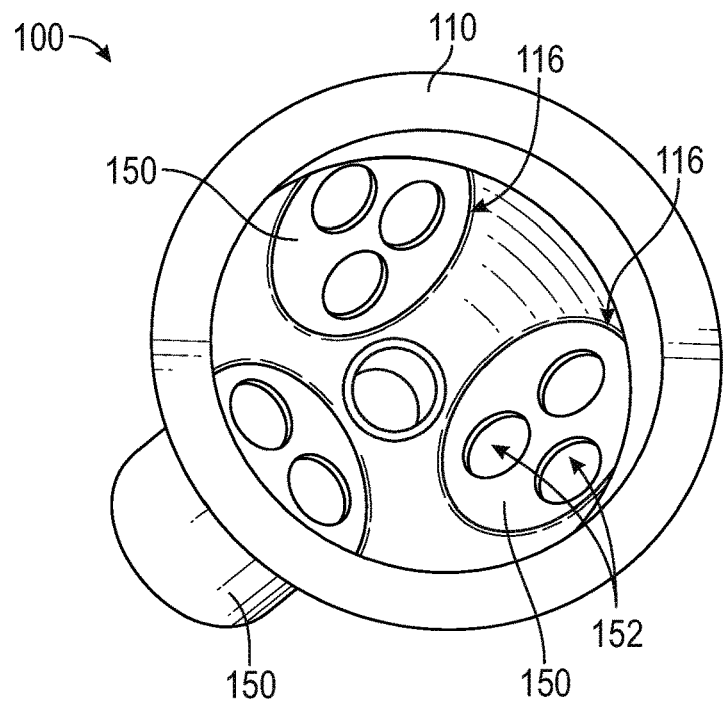
FIG. 3 is a front view of the acetabular prosthesis of FIG. 2 according to at least one example of the present disclosure.

Referring now to FIGS. 2 and 3, one exemplary acetabular prosthesis 100 is shown that can eliminate the need for providing a surgeon with many different acetabular prostheses during a hip implantation or revision procedure. Acetabular prosthesis 100 can include a shell 110 that can have an outer shape or profile that can be dome-shaped or hemi-spherical in shape, although other shapes are also contemplated. The shell 110 can include a plurality of through bores 116 arrayed throughout the shell 110. Although three through bores 116 are shown, any suitable number can be included. Although generally cylindrically-shaped through bores are shown, any other suitable shape is also contemplated, such as cube-shaped, cone-shaped, pyramid-shaped, spherical-shaped, prism-shaped, or any other three-dimensional shape.

As shown in FIGS. 2-3, acetabular prosthesis 100 can include one or more augments 150 that can be received within and fill the plurality of through bores 116. The augments 150 can have many different shapes and sizes that can be optimized to accommodate different types of bone defects in an acetabulum. The shape of augments in the figures is shown to be generally cylindrically-shaped. However, the shape is not limited to cylindrically-shaped augments, and the augments can be any suitable shape that fits within any shape of through bore or that accommodates a bone defect, such as cube-shaped, cone-shaped, pyramid-shaped, spherical-shaped, prism-shaped, or any other three-dimensional shape.

Each of the augments 150 can include one or more through holes 152 for additional fixation using bone screws, for example. The augments 150 can be selected by a surgeon such that they are able to engage patient-specific boney anatomy of the acetabulum, or hip socket, near an exterior of the acetabular prosthesis 100. The augments 150, therefore, can selectively change or modify a final external geometrical shape of the shell 110 of the acetabular prosthesis 100 after manufacture of the prosthesis 100, but prior to implantation. Further, a central bore 118 can be formed through the shell 110, and can be used to assist with implantation of the shell 110, such as by accommodating an implantation tool (not shown).

Figure 4:
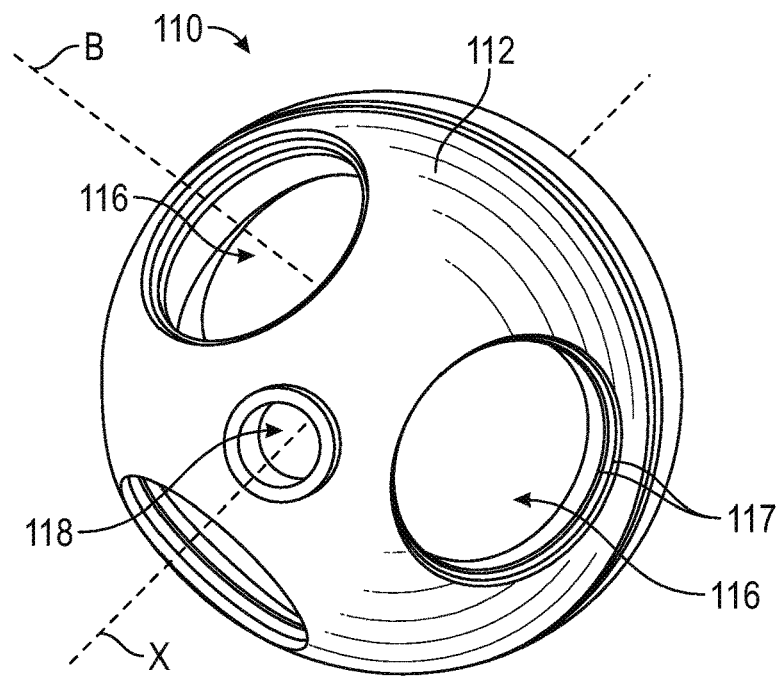
FIG. 4 is a backside view of a shell portion of an acetabular prosthesis according to at least one example of the present disclosure.
Figure 5:
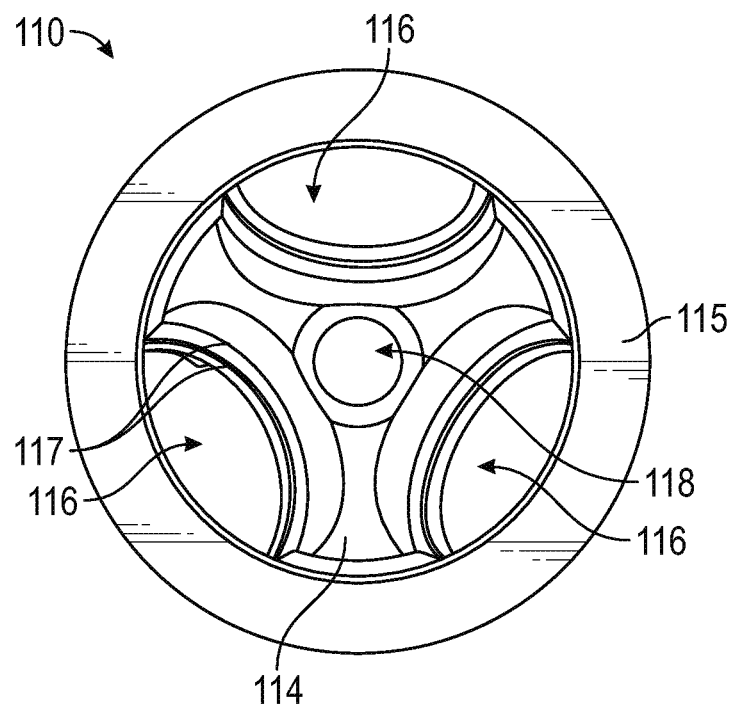
FIG. 5 is a front view of the shell portion of FIG. 4 according to at least one example of the present disclosure.
Figure 6:
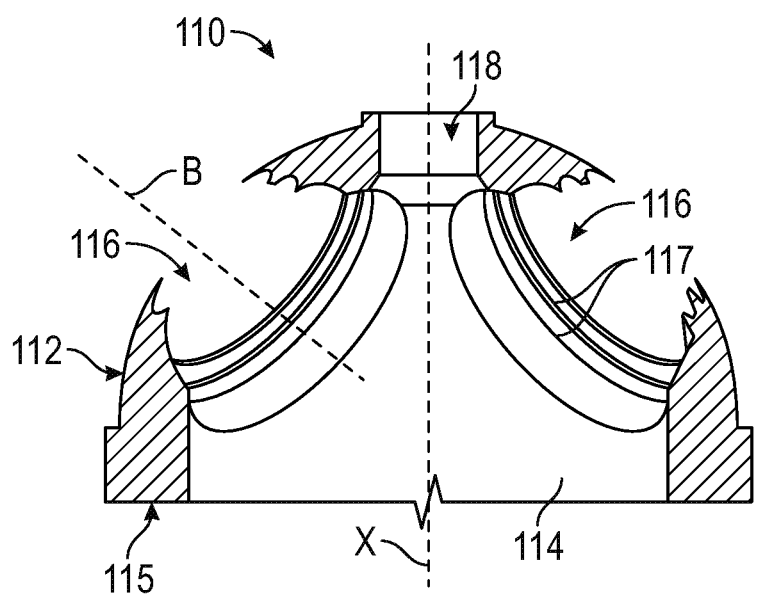
FIG. 6 is a cross-sectional view of the shell portion of FIGS. 4-5 according to at least one example of the present disclosure.

FIG. 4 illustrates a backside view of the acetabular prosthesis shell 110 without augments, FIG. 5 illustrates a front view of the shell 110, and FIG. 6 illustrates a cross-sectional view of the shell 110. The acetabular shell 110 can include an outer surface 112 and an inner surface 114. A peripheral surface or rim 115 (see FIG. 5) can be defined between the outer surface 112 and the inner surface 114. As illustrated, the shell 110 can include a plurality of through bores 116. The through bores 116 can be threaded bores (such as with a thread 117) extending from the outer surface 112 to the inner surface 114 of the shell 110. As illustrated, the shell 110 can include three threaded, through bores 116 formed around a central axis X. The central axis X can extend through a central bore 118. Each of the threaded through bores 116 can be formed angularly offset from each other, such as spaced about 120° apart, as shown. Further, the central bore 118 can be formed through the outer surface 112 of the shell 110, and can be used to accommodate an implantation tool to assist with implantation of the shell 110. The number and location of the through bores 116 can vary from those shown in the embodiment of FIGS. 4-6, however.

Acetabular shell 110 can be formed of a biocompatible metal, such as titanium. The outer surface 112 of the shell 110 can be treated to facilitate bone ingrowth or fixation to bone cement, such as for example, by a porous coating. A porous metal structure can be used for the coating. An example of such an open porous metal material can include REGENEREX® porous titanium construct, or Osseo Ti™. Another example of an open porous metal structure that can be used is produced using Trabecular Metal™ Technology available from Zimmer, Inc., of Warsaw, Ind. Trabecular Metal™ is a trademark of Zimmer, Inc. Such a material may be formed from a reticulated vitreous carbon foam substrate which is infiltrated and coated with a biocompatible metal, such as tantalum, by a chemical vapor deposition ("CVD") process in the manner disclosed in detail in U.S. Pat. No. 5,282,861 and in Levine, B. R., et al., "Experimental and Clinical Performance of Porous Tantalum in Orthopedic Surgery", Biomaterials 27 (2006) 4671-4681, the disclosures of which are expressly incorporated herein by reference.

A selected number, such as one or more, of the through bores 116 may receive an augment 150 that can fit within and fill the through bore 116 and that may or may not extend beyond the outer surface 112. For example, one or more of a selected type of augment (such as 150, 250, 350, 450 or 551, as illustrated in FIGS. 7-13, and described below), can be used to change the external geometry of the shell 110 in order to accommodate defects in a patient's acetabulum. The types, shapes and sizes of augments, such as 150, 250, 350, 450 or 551, that are possible for use in acetabular prosthesis 100 or other acetabular prostheses with through bores are varied and numerous. All possible configurations of such contemplated augments are not shown in the present disclosure.

Figure 7:
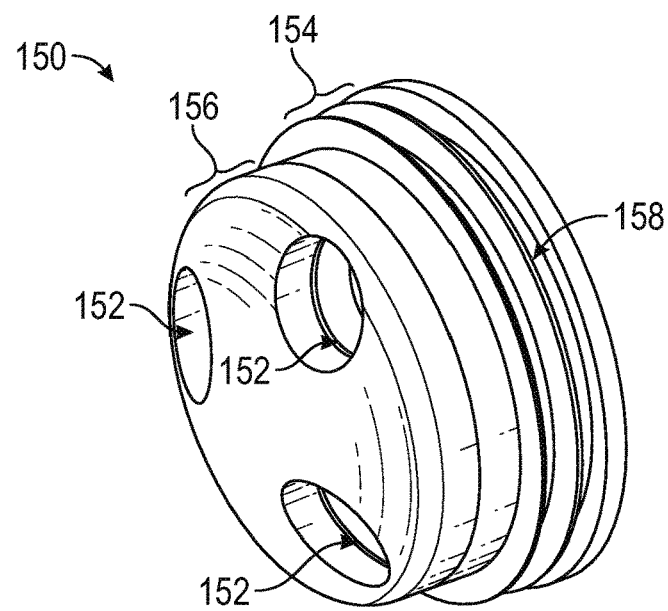
FIG. 7 is a perspective view of an augment portion of an acetabular prosthesis according to at least one example of the present disclosure.
Figure 8:
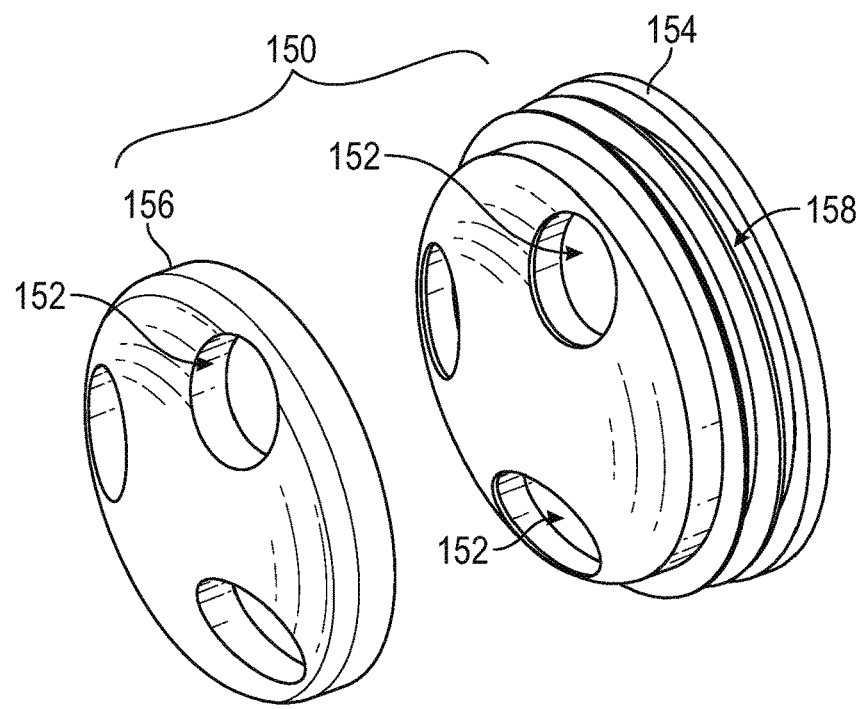
FIG. 8 is an exploded view of the augment portion of FIG. 7 according to at least one example of the present disclosure.

FIG. 7 shows a perspective view of augment 150 and FIG. 8 shows an exploded view of augment 150 in which a solid portion 154 is exploded from a porous coating portion 156. The augment 150 can include such a porous coated portion 156 that is coextensive with an external porous coated surface of an acetabular shell (not shown) or can extend to a location beyond the outer surface of the shell (not shown) after positioning the augment 150 therein. The solid portion 154 of the augment 150 can include an external screw thread 158.

Augment 150 can be held in place in a corresponding through bore of an acetabular shell, such as shell 110 in FIG. 6, by any suitable fastening means. As shown in FIG. 6, the through bore 116 can include at least one screw thread 117 inside the through bore 116, and at least one counterpart external screw thread 158 can be located on the augment 150 (FIG. 7). The fastening means used to attach, couple or fasten the augment 150, for example, to shell 110 can be continuous or discrete threads along at least a portion of an internal surface of the shell 110 and an external surface of the augment 150, for example. Such threads can be in the form of a single, double or multiple helical threads.

The threaded augment 150 can be coupled to the acetabular shell 110 such that it is co-extensive with an inner surface 114 and an outer surface 112 of the acetabular shell 110. As shown, the augment 150 can include a portion that extends beyond or outside the thorough bore 116 in order to alter or modify the external geometry of a shell into which it is incorporated, such as shell 110 in FIGS. 4-6.

Augment 150 can include a plurality of through holes 152 formed there through. Each of the through holes 152 formed through the augment 150 can allow for receiving a screw or bone fixation member to assist in fixation of the acetabular prosthesis, or shell, into an acetabulum into which it is incorporated. Following implantation of a hip prosthesis including the acetabular prosthesis described herein, for example, fixation can be enhanced through the use of bone screws. Bone screws can extend though augments including through holes, such as augment 150.

The through holes 152 of the augment 150 can be threaded or non-threaded. Thus, it can be possible to use locking screws, non-locking screws, or a combination thereof. In an example, the bone screw and/or the through hole 152 can be configured to allow for polyaxial insertion of the bone screw through the through hole 152 along a trajectory selected by the surgeon. There can be any suitable number of such through holes 152 in augment 150, for example.

Figure 9:
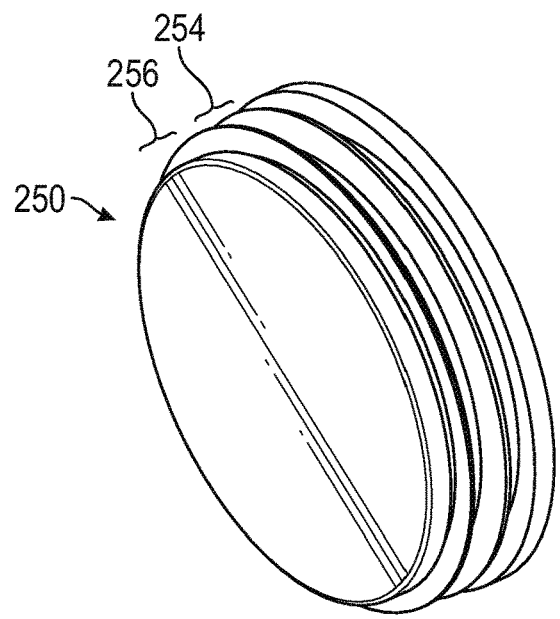
FIG. 9 is a perspective view of an augment portion of an acetabular prosthesis according to at least one example of the present disclosure.
Figure 10:
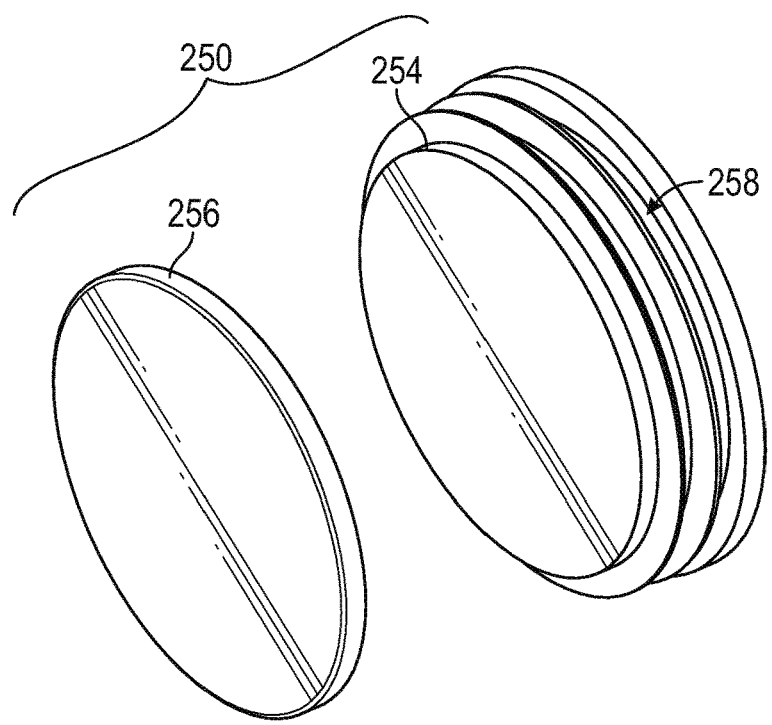
FIG. 10 is an exploded view of the augment portion of FIG. 9 according to at least one example of the present disclosure.

FIGS. 9-10 show another example of an augment 250 in a perspective view and an exploded view, respectively. Augment 250 is void of any through holes. The augment 250 can extend within a through bore in an acetabular shell into which it is incorporated. The augment 250 can be sized and shaped such that it can be co-extensive with an inner surface, an outer surface, or both an inner and outer surface of an acetabular shell.

Augment 250 may be threaded or non-threaded. As shown in FIGS. 9-10, augment 250 can include an exterior thread 258. The augment 250 can have a solid portion 254 and an external porous coated portion 256. In FIG. 10, the porous coated portion 256 is illustrated exploded from the solid portion 254. FIG. 9 illustrates the porous coated portion 256 and solid portion 254 together as a single member or an assembly. Augment 250 can be used to fill a through bore in a shell.

Figure 11:
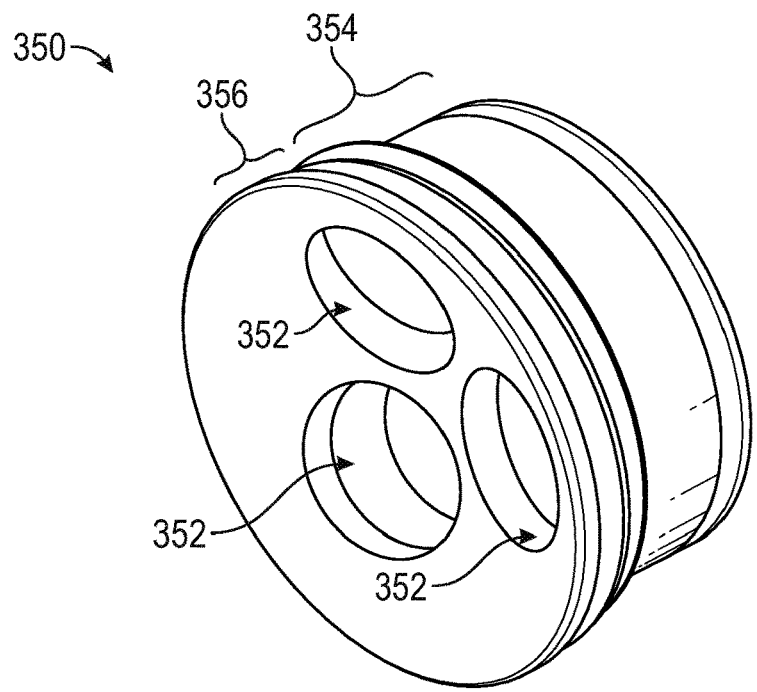
FIG. 11 is a perspective view of an augment portion of an acetabular prosthesis according to at least one example of the present disclosure.

FIG. 11 shows another example of an augment 350, which can include a plurality (three shown) of through bores 352. Although shown in one-piece, augment 350 can alternatively include a solid portion 354 and a porous coated portion 356, which are separate components and that can be assembled. Augment 350 differs from augment 150, as in FIGS. 7-8, in that a solid portion 354 and porous coated portion 356 have a concave shape as compared to a convex shape in augment 150 (FIGS. 7-8). Therefore, augment 350 can accommodate a boney protrusion, for example, in an acetabulum. Also, the through holes 352 in augment 350 are located radially inward and closer together than the through holes 152 in augment 150. The locations of the through holes 352 are exemplary, however, and other suitable locations and arrangements are contemplated.

Augment 350 does not include an external thread, and provides an example of an augment utilizing an alternative fastening means from a thread. For example, augment 350 can be attached to a shell using locking tapers (on the shell and the augment 350). Alternatively, the porous coated portion 356 can include a thread (not shown), while the solid portion can be smooth. The porous coated portion 356 with the thread can act as a cap fastening both the porous coated portion 356 and the solid portion 354 to a shell. The solid portion 354 can be fit into a hole (or opening or through bore), for example, in a shell (not shown), and the porous coated portion 365 can be fastened to the shell and can act to keep the solid portion 354 in place.

Figure 12:
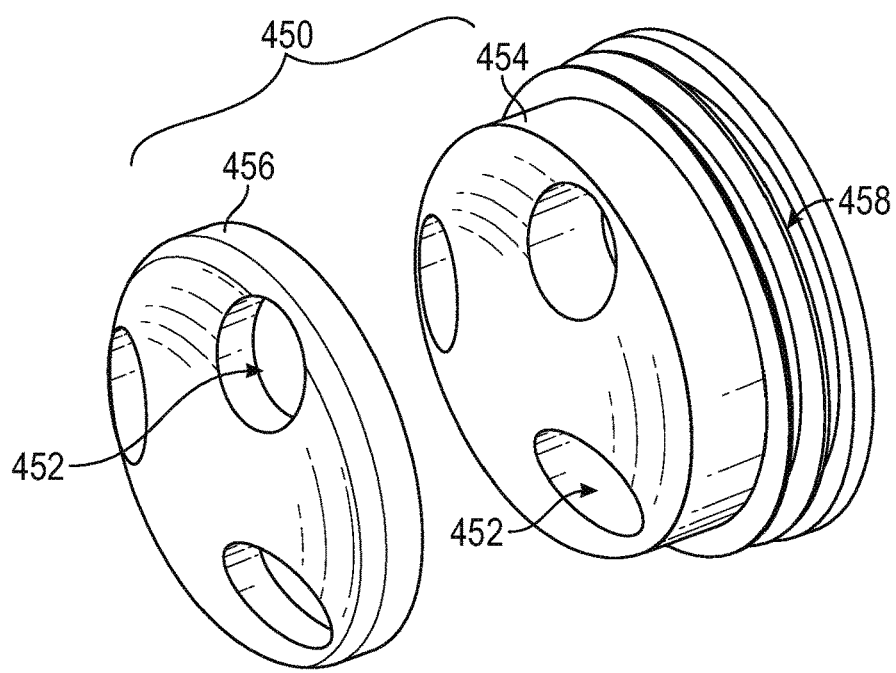
FIG. 12 is an exploded view of an augment portion of an acetabular prosthesis according to at least one example of the present disclosure.

FIG. 12 shows a further example of an augment 450, which includes a solid portion 454 and a porous coated portion 456, which are shown in an exploded view. The solid portion 454 and porous coated portion 456 both include through holes 452 for accommodating one to three bone screws, for example. The solid portion 454 of the augment 450 can have a length that is greater than that of augment 150, for example. Solid portion 454 can include at least one thread 458 for fastening to a shell.

Augments 150, 250, 350, and 450 can be constructed of a biocompatible metal such as titanium, a titanium alloy, or tantalum, for example. The augments can be made of the same material as the shell, but can be manufactured separately from the shell. At least a portion of augments 150, 250, 350, and 450, as well as at least a portion of a shell into which they are incorporated, can have a porous coating. The porous coating can provide a surface of interconnected three-dimensional pores with which bone or bone cement can achieve a secure, stable mechanical interlock. Some examples of materials that can be used for such a porous coating can include: a titanium porous plasma spray, or Osseo Ti™ or Trabecular Metal™, which is described herein above.

A plurality of augments, such as 150, 250, 350, and 450, can be provided that include a variable dimension, such as a variable length. The length can be selected such that the augment may not or may extend beyond an external surface of a shell by different amounts. The length that an augment can extend beyond an external surface of the shell can be any length from 0 millimeters up to at least 1 millimeter to about 100 millimeters.

Augment 350, for example can have a solid portion 354 with a length of about 5 millimeters that has a diameter that can line up flush with an external surface of a shell while having a concave shape extending inwardly toward the shell. Augment 450, on the other hand, can include a length of a solid portion 454 that is about 8 millimeters, allowing some of the augment 450 to extend outside of an external surface of a shell (having a shell thickness of less than 8 millimeters, for example) into which it can be incorporated. It can be understood that a system of augments can include a plurality of lengths selected for various procedures. In addition to a system, or alternatively thereto, a patient specific length can be designed and manufactured, such as based on a pre-operative plan. The length can determine the distance that an augment surface extends from an external surface of a shell.

Figure 13:
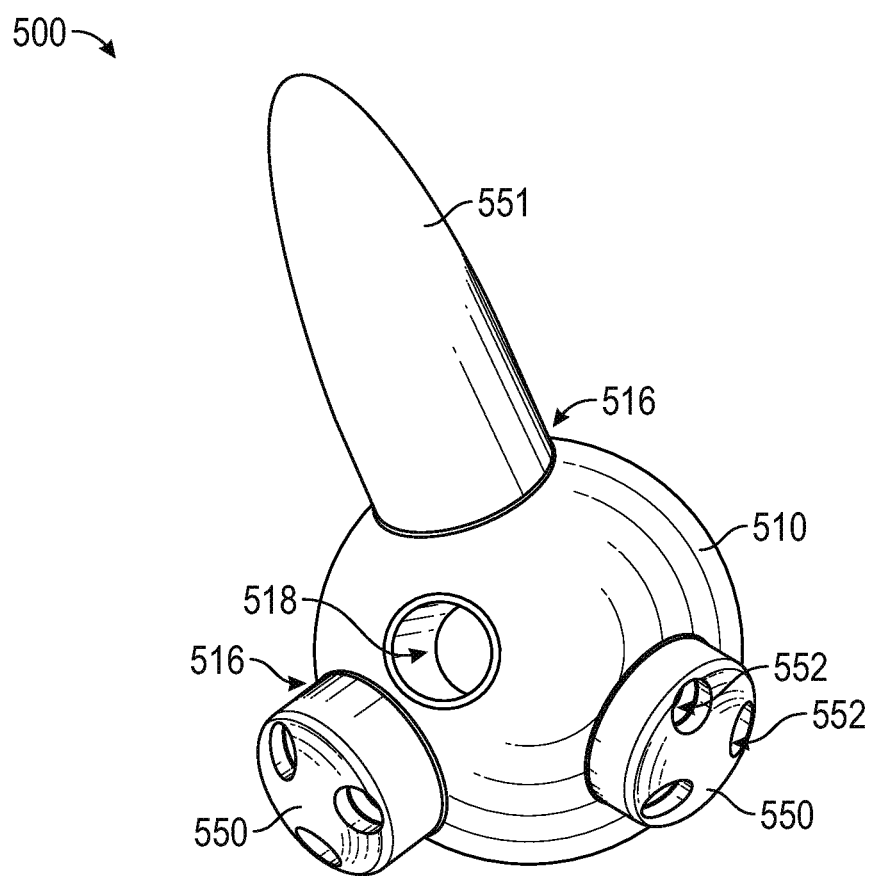
FIG. 13 is a backside view of an acetabular prosthesis according to at least one example of the present disclosure.

Augments, such as augments 150 in FIG. 2, can extend beyond the external surface of the shell 110 a few millimeters, such as shown, for example. However, another example can include at least one augment that extends beyond the external surface of the shell up to about 100 millimeters. The extension of such an augment can resemble a peg or spike, for example. FIG. 13 shows an acetabular prosthesis according to at least one example of the present disclosure including an augment 551 that resembles a peg or spike, and that extends beyond the external surface of the shell 510 up to about 100 millimeters. Augment 551, for example, can be used to fit against an area of significant bone loss in an acetabulum into which the shell 510 is implanted. A plurality of such augments, such as 551, can be used in acetabular prosthesis 500 as needed, for example.

Another additional feature of the exemplary augments can be that the augment can be adjustable along a longitudinal axis of the through bore once the augment is at least partially inserted within the through bore. FIGS. 4 and 6 show such a longitudinal axis B. The augment 150, for example, can be threaded into through bore 116 of shell 110. Adjustability of the augment 150 within the through bore 116 along the longitudinal axis B allows a surgeon to make adjustments to the amount of augment 150 that extends beyond the outer surface 112 of the shell 110 while performing revision surgery, for example. One example of how the augments may be adjustable is that they are able to be rotated and moved up and down along the longitudinal axis by interaction of complementary threads on the augments and the through bore. Other means for providing adjustability of the augments are contemplated however.

Augments can further include through holes, as shown in FIGS. 7-8 and 11-12, to assist in fixation, such as by passing a bone screw there through. The length of the augment can alter the final external geometry of a shell after positioning the augment through the shell. The external geometry can be changed to match or be selected for a specific patient. For example, a selected patient can have bone loss and the augment can be provided to replace some or all of the bone loss.

Therefore, a standard shell, such as 110, or a selection of shells, can be provided along with a selection of augments, such as 150, 250, 350, 450 or 551, of various types. A user, such as a surgeon, can then intraoperatively select one or more augments in order to provide a specific amount of augmentation, such as for bone loss replacement, during a procedure. The augments can also be selected based upon whether or not bone screws are desired in certain locations.

The shell 110 (FIGS. 4-6), for example, may be implanted into a prepared acetabulum 2 using a suitable tool. One example of a tool is a cup impactor from the G7 Acetabular System™, sold by Zimmer Biomet, Inc. The tool (not shown) can be configured for engagement with the central bore 118 in order to manipulate and place the shell 110 at the implant site. Once the acetabular shell 110 is placed in an appropriate position, the tool can be removed and the central bore 118 can be closed by means of a plug (not shown). The acetabular shell 100 can be aligned such that augments, such as 150, 250, 350, 450 or 551, for example, on the prosthesis, fit into bone defects, etc., and the prosthesis, or shell 110, can be implanted into the acetabulum 2. The shell 110 or acetabular prosthesis 100 (FIG. 1) can then be coupled to the acetabulum 2 by any appropriate known method. Augments may or may not include through holes (such as holes 152 in augment 150, in FIG. 7), through which bone screws can be inserted and fixed into bone.

Figure 14:
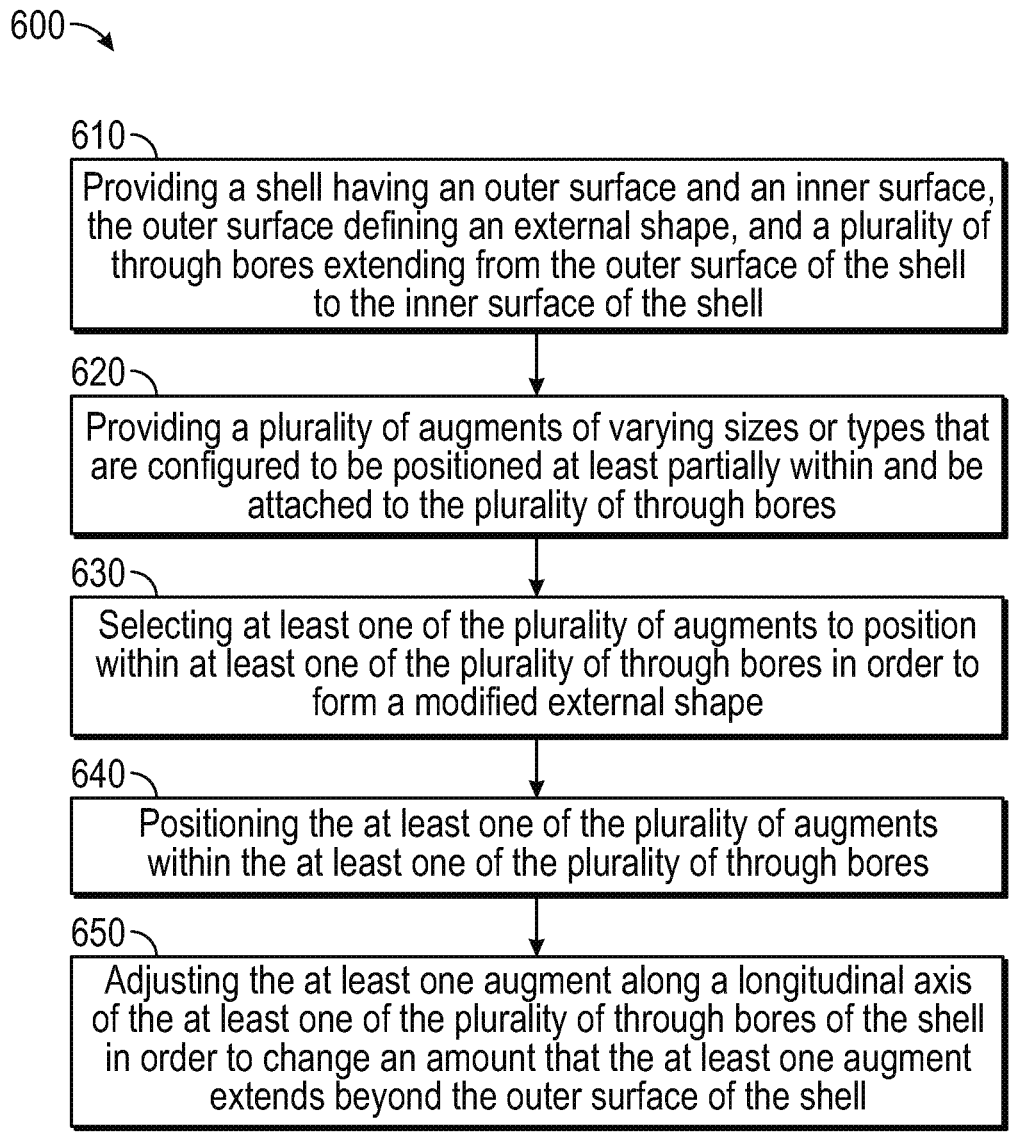
FIG. 14 is a flow chart illustrating a method of forming an acetabular prosthesis according to at least one example of the present disclosure.

FIG. 14 is a flow chart illustrating an embodiment of a method 500 of forming an acetabular prosthesis according to at least one example of the present disclosure. As set forth in FIG. 14, the method can begin at 610 by providing a shell having an outer surface, and an inner surface, the outer surface defining an external shape, and a plurality of through bores extending from the outer surface of the shell to the inner surface of the shell.

At 620, the method can also include providing a plurality of augments of varying sizes or types that are configured to be positioned at least partially within and be attached to the plurality of through bores. Further, at 630, the method can include selecting at least one of the plurality of augments to position within at least one of the plurality of through bores in order to form a modified external shape. In addition, at 640, the method can include positioning the at least one of the plurality of augments within the at least one of the plurality of through bores. The method can also include, at 650, adjusting the at least one augment along a longitudinal axis of the at least one of the plurality of through bores of the shell in order to change an amount that the at least one augment extends beyond the outer surface of the shell. In addition, the method can also include providing any of the embodiments of shells or augments, or features thereof, shown or described herein.

VARIOUS NOTES & EXAMPLES

To better illustrate the methods and apparatuses disclosed herein, a non-limiting list of embodiments is provided herein:

Example 1 includes an acetabular prosthesis including a shell having an outer surface and an inner surface, the outer surface defining an external shape; at least one through bore extending from the outer surface of the shell to the inner surface of the shell; and at least one augment configured to be positioned at least partially within the at least one through bore of the shell such that, in an assembled state, the shell and the at least one augment define a modified external shape.

Example 2 includes an acetabular prosthesis of example 1, wherein the at least one through bore comprises a plurality of through bores and the at least one augment comprises a plurality of augments of varying sizes or types that are configured to be positioned at least partially within and be attached to the plurality of through bores in order to form the modified external shape.

Example 3 includes an acetabular prosthesis of any one of examples 1-2, wherein in the assembled state the at least one augment extends from the inner surface of the shell to the outer surface of the shell.

Example 4 includes an acetabular prosthesis of any one of examples 1-2, wherein in the assembled state the at least one augment extends from the inner surface of the shell to a location beyond the outer surface of the shell.

Example 5 includes an acetabular prosthesis of any one of examples 1-4, wherein the at least one augment includes a thread and the at least one through bore includes a thread that is complementary to the thread on the at least one augment in order to attach the at least one augment to the at least one through bore.

Example 6 includes an acetabular prosthesis of any one of examples 1-5, wherein the at least one augment includes at least one through hole extending from an inner surface of the augment to an outer surface of the augment that is configured for receiving a bone screw.

Example 7 includes an acetabular prosthesis of any one of examples 1-6, wherein the at least one augment has an outer surface that is coextensive with the outer surface of the shell in the assembled state.

Example 8 includes an acetabular prosthesis of any one of examples 1-7, wherein the at least one augment includes three through bores that are angularly offset from each other by 120°.

Example 9 includes an acetabular prosthesis of any one of examples 1-8, wherein the at least one augment is configured to be adjusted along a longitudinal axis of the at least one through bore of the shell in order to change an amount that the at least one augment extends beyond the outer surface of the shell.

Example 10 includes an acetabular prosthesis of any one of examples 1-9, wherein the at least one augment includes a concave outer surface.

Example 11 includes an acetabular prosthesis of any one of examples 1-10, wherein the at least one augment includes a convex outer surface.

Example 12 includes an acetabular prosthesis of any one of examples 1-11, wherein the at least one through bore includes an inner surface that is smooth.

Example 13 includes an acetabular prosthesis of any one of examples 1-12, wherein the at least one augment includes an outer taper and the at least one through bore includes an inner taper such that the inner and outer tapers are configured to be complementary and to attach the at least one augment to the at least one through bore.

Example 14 includes an acetabular prosthesis of any one of examples 1-13, wherein at least one portion of the outer surface of the shell and at least one portion of an outer surface of the at least one augment has a porous coating.

Example 15 includes an acetabular prosthesis of any one of examples 1-14, in combination with a stem and a femoral head attached to the stem.

Example 16 includes an acetabular prosthesis including a shell having an outer surface and an inner surface, the outer surface defining an external shape; a plurality of through bores extending from the outer surface of the shell to the inner surface of the shell; and a plurality of augments of varying sizes or types configured to be at least partially positioned within and be attached to the plurality of through bores such that, in an assembled state, the shell and the plurality of augments define a modified external shape, wherein at least one of the plurality of augments extends from the inner surface of the shell to a location beyond the outer surface of the shell, and wherein at least one portion of the outer surface of the shell and at least one portion of an outer surface of at least one of the plurality of augments has a porous coating.

Example 17 includes a method of making an acetabular prosthesis, the method including: providing a shell having an outer surface and an inner surface, the outer surface defining an external shape, and a plurality of through bores extending from the outer surface of the shell to the inner surface of the shell; providing a plurality of augments of varying sizes or types that are configured to be positioned at least partially within and be attached to the plurality of through bores; and selecting at least one of the plurality of augments to position within at least one of the plurality of through bores in order to form a modified external shape.

Example 18 includes the method of example 17, wherein the at least one of the plurality of augments includes at least one through hole extending from an inner surface of the augment to an outer surface of the augment that is configured for receiving a bone screw.

Example 19 includes the method of any one of examples 17-18, further comprising: positioning the at least one of the plurality of augments within the at least one of the plurality of through bores.

Example 20 includes the method of any one of examples 17-19, further comprising: adjusting the at least one augment along a longitudinal axis of the at least one of the plurality of through bores of the shell in order to change an amount that the at least one augment extends beyond the outer surface of the shell.

Each of these non-limiting examples can stand on its own, or can be combined in various permutations or combinations with one or more of the other examples.

Although the subject matter of the present patent application has been described with reference to various embodiments, workers skilled in the art will recognize that changes can be made in form and detail without departing from the scope of the invention recited in the below claims.

The above detailed description includes references to the accompanying drawings, which form a part of the detailed description. The drawings show, by way of illustration, specific embodiments in which the present locator apparatus and methods can be practiced. These embodiments are also referred to herein as "examples."

The above detailed description is intended to be illustrative, and not restrictive. For example, the above-described examples (or one or more elements thereof) can be used in combination with each other. Other embodiments can be used, such as by one of ordinary skill in the art upon reviewing the above description. Also, various features or elements can be grouped together to streamline the disclosure. This should not be interpreted as intending that an unclaimed disclosed feature is essential to any claim. Rather, inventive subject matter can lie in less than all features of a particular disclosed embodiment. Thus, the following claims are hereby incorporated into the detailed description, with each claim standing on its own as a separate embodiment. The scope of the invention should be determined with reference to the appended claims, along with the full scope of equivalents to which such claims are entitled.

In this document, the terms "a" or "an" are used to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "about" and "approximately" or similar are used to refer to an amount that is nearly, almost, or in the vicinity of being equal to a stated amount.

In the appended claims, the terms "including" and "in which" are used as the plain-English equivalents of the respective terms "comprising" and "wherein." Also, in the following claims, the terms "including" and "comprising" are open-ended, that is, an apparatus or method that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The abstract is provided to allow the reader to quickly ascertain the nature of the technical disclosure. It is submitted with the understanding that it will not be used to interpret or limit the scope or meaning of the claims.

The claimed invention is:

1. An acetabular prosthesis, comprising:
   a shell having an outer surface and an inner surface, the outer surface defining an external shape;
   at least one through bore extending from the outer surface of the shell to the inner surface of the shell; and
   at least one augment configured to be positioned at least partially within the at least one through bore of the shell such that, in an assembled state, the shell and the at least one augment define a modified external shape;
   wherein the at least one augment includes an externally threaded surface and the at least one through bore includes an internally threaded surface that is complementary to the externally threaded surface on the at least one augment in order to attach the at least one augment to the at least one through bore; and
   wherein the at least one augment includes three internally threaded through bores that are angularly offset from each other by 120°, the through bores extending from an inner surface of the augment to an outer surface of the augment and configured for receiving a bone screw.

2. The acetabular prosthesis of claim 1, wherein the at least one through bore comprises a plurality of through bores and the at least one augment comprises a plurality of augments of varying sizes or types that are configured to be positioned at least partially within and be attached to the plurality of through bores in order to form the modified external shape.

3. The acetabular prosthesis of claim 1, wherein in the assembled state the at least one augment extends from the inner surface of the shell to the outer surface of the shell.

4. The acetabular prosthesis of claim 1, wherein in the assembled state the at least one augment extends from the inner surface of the shell to a location beyond the outer surface of the shell.

5. The acetabular prosthesis of claim 1, wherein the at least one augment has an outer surface that is coextensive with the outer surface of the shell in the assembled state.

6. The acetabular prosthesis of claim 1, wherein the at least one augment is configured to be adjusted along a longitudinal axis of the at least one through bore of the shell in order to change an amount that the at least one augment extends beyond the outer surface of the shell.

7. The acetabular prosthesis of claim 1, wherein the at least one augment includes a concave outer surface.

8. The acetabular prosthesis of claim 1, wherein the at least one augment includes a convex outer surface.

9. The acetabular prosthesis of claim 1, wherein the at least one augment includes an outer taper and the at least one through bore includes an inner taper such that the inner and outer tapers are configured to be complementary and to attach the at least one augment to the at least one through bore.

10. The acetabular prosthesis of claim 1, wherein at least one portion of the outer surface of the shell and at least one portion of an outer surface of the at least one augment has a porous coating.

11. The acetabular prosthesis of claim 1, in combination with a stem and am femoral head attached to the stem.

12. An acetabular prosthesis, comprising:
    a shell having an outer surface and an inner surface, the outer surface defining an external shape;
    a plurality of through bores extending from the outer surface of the shell to the inner surface of the shell; and
    a plurality of augments of varying sizes or types configured to be at least partially positioned within and be attached to the plurality of through bores such that, in an assembled state, the shell and the plurality of augments define a modified external shape,
    wherein at least one of the plurality of augments extends from the inner surface of the shell to a location beyond the outer surface of the shell, wherein at least one of the plurality of augments includes a plurality of through bores configured to receive a bone fixation member, and wherein at least one portion of the outer surface of the shell and at least one portion of an outer surface of at least one of the plurality of augments has a porous coating.

13. An acetabular prosthesis, comprising:
    a shell having an outer surface and an inner surface, the outer surface defining an external shape;
    at least one through bore extending from the outer surface of the shell to the inner surface of the shell; and
    at least one augment configured to be positioned at least partially within the at least one through bore of the shell such that, in an assembled state, the shell and the at least one augment define a modified external shape,
    wherein the at least one augment includes a plurality of through bores configured to receive a bone fixation member.

14. The acetabular prosthesis of claim 13, wherein the plurality of through bores in the at least one augment includes three through bores that are angularly off set from each other by 120°.

15. The acetabular prosthesis of claim 14, wherein in the assembled state the at least one augment extends from the inner surface of the shell to a location beyond the outer surface of the shell.

\* \* \* \* \*

UNITED STATES PATENT AND TRADEMARK OFFICE
CERTIFICATE OF CORRECTION

PATENT NO. : 10,159,572 B2  
APPLICATION NO. : 15/142740  
DATED : December 25, 2018  
INVENTOR(S) : Bailey et al.

Page 1 of 1

It is certified that error appears in the above-identified patent and that said Letters Patent is hereby corrected as shown below:

In the Claims

In Column 12, Line 36, in Claim 11, delete "am" and insert --a-- therefor

Signed and Sealed this  
Twenty-first Day of April, 2020

Andrei Iancu  
*Director of the United States Patent and Trademark Office*